United States Patent
Watson et al.

(10) Patent No.: US 11,211,163 B2
(45) Date of Patent: *Dec. 28, 2021

(54) METHODS AND SYSTEMS FOR PROVIDING THE PROXIMITY OF A PROCESS REQUIREMENT METRIC TO A SYSTEM PROCESS REQUIREMENT

(71) Applicant: Covidien LP, Mansfield, MA (US)

(72) Inventors: James Watson, Dunfermline (GB); Paul S. Addison, Edinburgh (GB); Keith Manning, Linlithgow (GB)

(73) Assignee: COVIDIEN LP, Mansfield, MA (US)

(*) Notice: Subject to any disclaimer, the term of this patent is extended or adjusted under 35 U.S.C. 154(b) by 905 days.

This patent is subject to a terminal disclaimer.

(21) Appl. No.: 15/888,328

(22) Filed: Feb. 5, 2018

(65) Prior Publication Data

US 2018/0158550 A1 Jun. 7, 2018

Related U.S. Application Data

(63) Continuation of application No. 14/717,594, filed on May 20, 2015, now Pat. No. 9,910,960.
(Continued)

(51) Int. Cl.
*G01N 33/48* (2006.01)
*G01N 33/50* (2006.01)
(Continued)

(52) U.S. Cl.
CPC .............. *G16H 40/63* (2018.01); *A61B 5/746* (2013.01); *G16H 50/20* (2018.01); *A61B 5/021* (2013.01);
(Continued)

(58) Field of Classification Search
CPC ........ G16H 40/63; G16H 50/20; A61B 5/746; A61B 5/021; A61B 5/14551; A61B 2560/0223; A61B 5/02416
See application file for complete search history.

(56) References Cited

U.S. PATENT DOCUMENTS 5,253,645 A * 10/1993 Friedman et al.
9,910,960 B2 * 3/2018 Watson .................. A61B 5/746
(Continued)

FOREIGN PATENT DOCUMENTS

CN 1672631 A * 9/2005

OTHER PUBLICATIONS

English machine translation of CN-1672631A. (Year: 2020).*
(Continued)

*Primary Examiner* — Russell S Negin
(74) *Attorney, Agent, or Firm* — Shumaker & Sieffert, P.A.

(57) ABSTRACT

Methods and systems are presented for indicating the proximity of a process requirement metric to a corresponding system process requirement in a physiological monitor. Metrics are determined based on a received physiological signal, such as a PPG signal. At least one of the metrics is compared to a corresponding system process requirement, such as a threshold, which can be used to trigger a system process, such as an alarm, a recalibration, or a measurement. The proximity of the metric to the corresponding system process requirement is calculated and indicated. Indicating the proximity to a system process requirement may provide valuable information to clinicians and allow them to manually trigger system processes, such as measurements or recalibrations, when a metric is close to a system process requirement for a significant period of time.

19 Claims, 7 Drawing Sheets

Related U.S. Application Data

(60) Provisional application No. 62/012,206, filed on Jun. 13, 2014.

(51) Int. Cl.
| | |
|---|---|
| *G16H 40/63* | (2018.01) |
| *A61B 5/00* | (2006.01) |
| *G16H 50/20* | (2018.01) |
| *A61B 5/024* | (2006.01) |
| *A61B 5/021* | (2006.01) |
| *A61B 5/1455* | (2006.01) |

(52) U.S. Cl.
CPC ....... *A61B 5/02416* (2013.01); *A61B 5/14551* (2013.01); *A61B 2560/0223* (2013.01)

(56) References Cited

U.S. PATENT DOCUMENTS

| | | |
|---|---|---|
| 2008/0167564 A1 | 7/2008 | Hete et al. |
| 2012/0050045 A1* | 3/2012 | Hively ............... G06K 9/00536 340/573.1 |
| 2012/0136261 A1* | 5/2012 | Sethi .................... A61B 5/1495 600/485 |
| 2012/0253141 A1 | 10/2012 | Addison et al. |
| 2013/0079656 A1* | 3/2013 | Dripps ............... A61B 5/14551 600/529 |

OTHER PUBLICATIONS

Golub et al. "Molecular classification of cancer: Class discovery and class prediction by gene expression monitoring". Science, vol. 286, Oct. 15, 1999, 8 pp.

Prosecution History from U.S. Appl. No. 14/717,594, dated Mar. 9, 2017 through Dec. 22, 2017, 53 pp.

* cited by examiner

METHODS AND SYSTEMS FOR PROVIDING THE PROXIMITY OF A PROCESS REQUIREMENT METRIC TO A SYSTEM PROCESS REQUIREMENT

This application is a continuation of U.S. patent application Ser. No. 14/717,594, filed May 20, 2015, which claims the benefit of U.S. Provisional Application No. 62/012,206, filed Jun. 13, 2014, each of which is hereby incorporated by reference herein in its entirety.

FIELD OF THE DISCLOSURE

The present disclosure relates to a physiological monitoring system, and more particularly relates to indicating the proximity of a process requirement metric to a corresponding system process requirement of a physiological monitoring system.

SUMMARY

It may be advantageous to inform a clinician of the proximity of a particular monitored metric or parameter to a corresponding threshold which triggers a system process when the value of the monitored metric or parameter meets or crosses the corresponding threshold. For example, such an indication of proximity may inform a clinician that a physiological monitoring system has been close to automatically triggering a measurement for a number of minutes, and the clinician may manually take a measurement in response. The present disclosure provides an indication to a clinician of how close a process requirement metric, or any other suitable monitored metric or parameter, is to system process requirement. In some embodiments, a system process requirement of the present disclosure may be a threshold, and may trigger a system process when the value of a process requirement metric meets or crosses the system process requirement. A system process may be a recalibration or a measurement in a non-invasive blood pressure monitoring system, or an alarm in a pulse oximetry system.

In some embodiments, a method includes receiving at least one physiological signal from the subject and determining a change in value of at least one metric based at least in part on the received physiological signal. The method includes calculating a proximity of the change in value of the metric to a corresponding threshold and indicating the proximity.

In some embodiments, a system includes an input configured to receive a physiological signal, for example, a photoplethysmograph (PPG) signal, and microprocessor circuitry configured to determine a value of at least one process requirement metric based at least in part on the received physiological signal, and calculate a proximity of the value of the process requirement metric to a corresponding threshold. An output module is configured to indicate the proximity.

In some embodiments, a system includes an input configured to receive a physiological signal, for example, a photoplethysmograph (PPG) signal, and microprocessor circuitry is configured to determine a value of at least one process requirement metric based at least in part on the received physiological signal, compare the value of the process requirement metric to a corresponding threshold and output a comparison signal based on the comparison, where the comparison signal is used to trigger a process when the value of the process requirement metric meets or crosses the corresponding threshold, and calculate a proximity of the value of the process requirement metric to the corresponding threshold. The system includes an output module configured to indicate the proximity.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
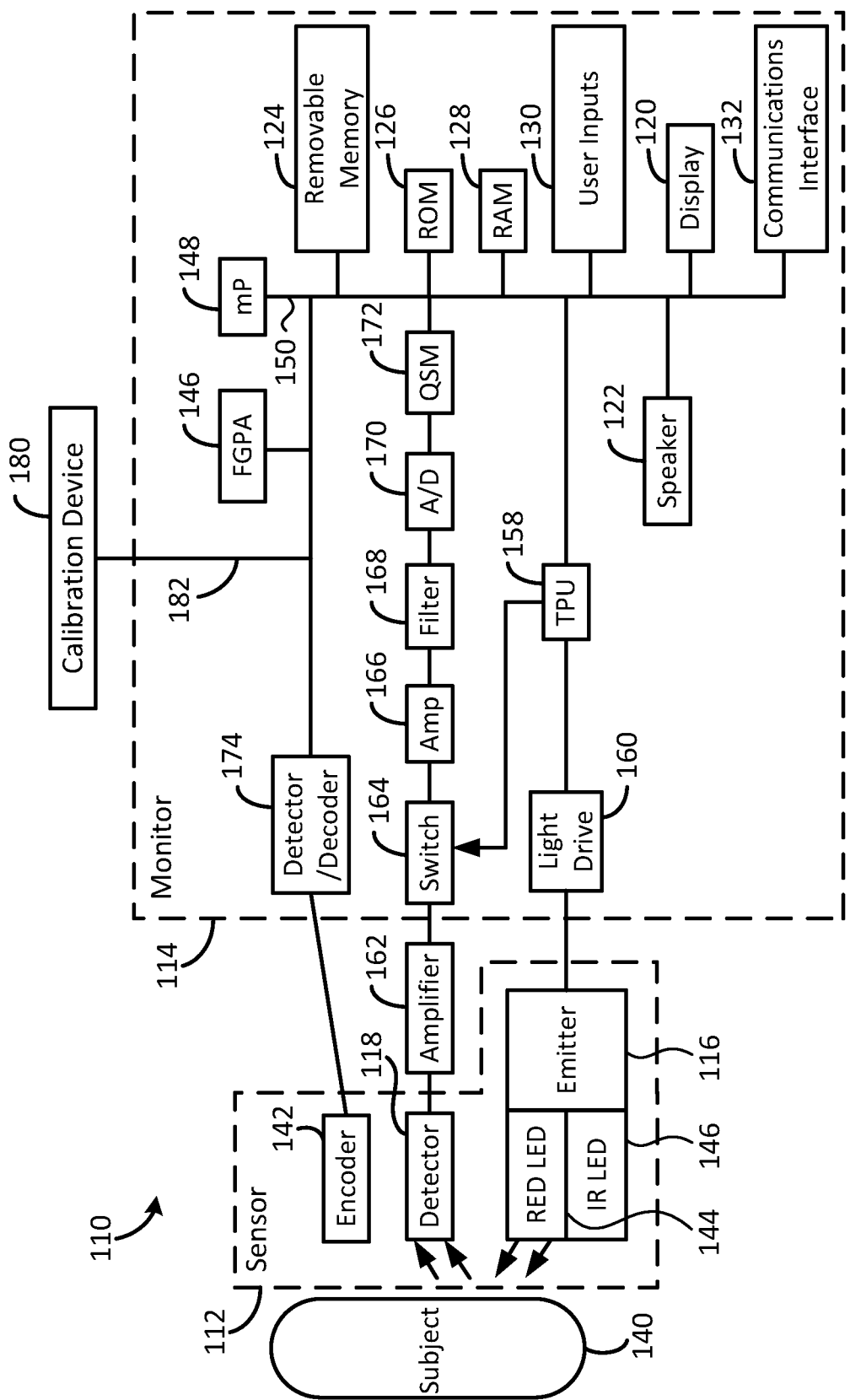
FIG. 1 is a block diagram of an illustrative physiological monitoring system in accordance with some embodiments of the present disclosure.

A threshold can be used for triggering a process within a system. Such processes may include, for example, alarms, recalibration processes, or measurement processes. In certain situations, it may be advantageous to inform a clinician, or other user, of the proximity of a monitored metric or parameter to a corresponding threshold which triggers such a process. The present disclosure is directed towards indicating the proximity of a process requirement metric, such as any suitable monitored metric or parameter, to a corresponding system process requirement (e.g., a threshold) of a physiological monitor. The physiological monitor may determine a value of one or more process requirement metrics or a change in value of one or more process requirement metrics for a received physiological signal (e.g., a PPG signal). For example, a process requirement metric may be the pulse period of a PPG signal. The physiological monitor may calculate the proximity of the value or change in value of the process requirement metric to a corresponding system process requirement. When the process requirement metric reaches a value that is equal to or has crossed the system process requirement metric, a system process may be triggered, for example, an alarm, a recalibration, a measurement, any other suitable system process, or any combination thereof. The physiological monitor may indicate the proximity to the system process requirement, for example, using a bar display, a color changing display, aural cues, any other suitable indication technique, or any combination thereof.

In some embodiments, the physiological monitor of the present disclosure may be a non-invasive blood pressure (NIBP) monitoring system such as a continuous non-invasive blood pressure (CNIBP) monitoring system. A CNIBP monitoring system continuously measures a subject's blood pressure but typically requires recalibration. Recalibration of a CNIBP monitoring system may occur periodically at fixed intervals, in response to a threshold which is met or crossed, or as specified by a clinician. In some embodiments, pulse oximetry may be utilized in a CNIBP monitoring system. The physiological monitor is not limited to a CNIBP monitoring system, and may instead be a NIBP monitoring system which may perform periodic measurements of a subject's blood pressure without continuously updating blood pressure. NIBP system measurements may be performed periodically at fixed intervals, in response to a threshold which is met or crossed, or as specified by a clinician.

In some embodiments, the physiological monitor of the present disclosure may be an oximeter. An oximeter is a medical device that may determine the oxygen saturation of the blood. One common type of oximeter is a pulse oximeter, which may indirectly measure the oxygen saturation of a subject's blood (as opposed to measuring oxygen saturation directly by analyzing a blood sample taken from the subject). A pulse oximeter may be included in physiological monitoring systems that measure and display various blood flow characteristics including, but not limited to, the oxygen saturation of hemoglobin in arterial blood. Such physiological monitoring systems may also measure and display additional physiological parameters, such as a subject's pulse rate, respiration rate, or blood pressure.

An oximeter may include a light sensor that is placed at a site on a subject, typically a fingertip, toe, forehead or earlobe, or in the case of a neonate, across a foot. The oximeter may use a light source to pass light through blood perfused tissue and photoelectrically sense the transmission of the light in the tissue. In addition, locations which are not typically understood to be optimal for pulse oximetry may serve as suitable sensor locations for blood pressure monitoring, including any location on the body that has a strong pulsatile arterial flow. For example, additional suitable sensor locations include, without limitation, the neck to monitor carotid artery pulsatile flow, the wrist to monitor radial artery pulsatile flow, the inside of a subject's thigh to monitor femoral artery pulsatile flow, the ankle to monitor tibial artery pulsatile flow, and around or in front of the ear. Suitable sensors for these locations may include sensors for sensing attenuated light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as a photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

FIG. 1 is a block diagram of an illustrative physiological monitoring system 110 in accordance with some embodiments of the present disclosure. System 110 may include a sensor 112 and a monitor 114 for generating and processing physiological signals of a subject 140. In some embodiments, system 110 may be coupled to subject 140. In some embodiments, sensor 112 and monitor 114 may be part of a blood pressure monitoring system and/or an oximeter.

Sensor unit 112 may include emitter 116, detector 118, and encoder 142. In the embodiment shown, emitter 116 may be configured to emit at least two wavelengths of light (e.g., red and IR) into the tissue of subject 140. For example, in the embodiment shown, emitter 116 may include a red light emitting light source such as RED light emitting diode (LED) 144 and an IR light emitting light source such as IR LED 146 for emitting light into the tissue of subject 140 to generate physiological signals. In some embodiments, the red wavelength may be between about 600 nm and about 700 nm, and the IR wavelength may be between about 800 nm and about 1000 nm. It will be understood that emitter 116 may include any number of light sources with any suitable characteristics. In embodiments where an array of sensors is used in place of single sensor 112, each sensor may be configured to emit a single wavelength. For example, a first sensor may emit only a red light while a second may emit only an IR light. In another example, the wavelengths of light used are selected based on the specific location of the sensor.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 118 may be chosen to be specifically sensitive to the chosen targeted energy spectrum of the emitter 116, the hemoglobin absorption profile, or both.

In some embodiments, detector 118 may be configured to detect the intensity of light at the red and IR wavelengths. In some embodiments, an array of sensors may be used and each sensor in the array may be configured to detect an intensity of a single wavelength. In operation, light may enter detector 118 after being attenuated (e.g., absorbed, scattered) by the tissue of subject 140. Detector 118 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detector 118. After converting the received light to an electrical signal, detector 118 may send the signal to monitor 114, where the signal may be processed and physiological parameters may be determined (e.g., based on the absorption of the red and IR wavelengths in the tissue of subject 140).

In some embodiments, encoder 142 may contain information about sensor 112, such as sensor type (e.g., whether the sensor is intended for placement on a forehead or digit), the wavelengths of light emitted by emitter 116, power requirements or limitations of emitter 116, or other suitable information. This information may be used by monitor 114 to select appropriate algorithms, lookup tables and/or calibration coefficients stored in monitor 114 for calculating the subject's physiological parameters.

In some embodiments, encoder 142 may contain information specific to subject 140, such as, for example, the subject's age, weight, and diagnosis. Information regarding a subject's characteristics may allow monitor 114 to determine, for example, subject-specific threshold ranges in which the subject's physiological parameter measurements should fall and to enable or disable additional physiological parameter algorithms. This information may also be used to select and provide coefficients for equations from which, for example, oxygen saturation, pulse rate, blood pressure, and other measurements may be determined based on the signal or signals received at sensor unit 112. For example, some pulse oximetry sensors rely on equations to relate an area under a portion of a PPG signal corresponding to a physiological pulse to determine blood pressure. These equations may contain coefficients that depend upon a subject's physiological characteristics as stored in encoder 142. Encoder 142 may, for instance, be a coded resistor which stores values corresponding to the type of sensor unit 112 or the type of each sensor in the sensor array, the wavelengths of light emitted by emitter 116 on each sensor of the sensor array, and/or the subject's characteristics. In some embodiments, encoder 142 may include a memory on which one or more of the following information may be stored for communication to monitor 114: the type of the sensor unit 112; the wavelengths of light emitted by emitter 116; the particular wavelength each sensor in the sensor array is monitoring; a signal threshold for each sensor in the sensor array; any other suitable information; or any combination thereof. In some embodiments, encoder 142 may include an identifying component such as, for example, a radio-frequency identification (RFID) tag that may be read by decoder 174.

In some embodiments, signals from detector 118 and encoder 142 may be transmitted to monitor 114. In the embodiment shown, monitor 114 may include a general purpose microprocessor 148, FPGA 146, or both, connected to an internal bus 150. In some embodiments, monitor 114 may include one or more microprocessors, digital signal processors (DSPs), or both. Microprocessor 148 may be adapted to execute software, which may include an operating system and one or more applications, as part of performing the functions described herein. Also connected to bus 150 may be a read-only memory (ROM) 126, a random access memory (RAM) 128, removable memory 124, user inputs 130, display 120, and speaker 122.

RAM 128, ROM 126, and removable memory 124 are provided as illustrative examples (e.g., communications interface 132, flash memory, digital logic array, field programmable gate array (FPGA), or any other suitable memory) and are not provided by way of limitation. Any suitable computer-readable media may be used in the system for data storage. Computer-readable media are capable of storing information that can be interpreted by microprocessor 148, FPGA 146, or both. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, writable and non-writable, and removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 158 may provide timing control signals to light drive circuitry 160, which may control when emitter 116 is illuminated and multiplexed timing for RED LED 144 and IR LED 146. TPU 158 may also control the gating-in of signals from detector 118 through amplifier 162 and switching circuit 164. These signals are sampled at the proper time, depending upon which light source is illuminated. In some embodiments, microprocessor 148, FPGA 146, or both, may de-multiplex the signal from detector 118 using de-multiplexing techniques such as time-division, frequency-division, code division, or any other suitable de-multiplexing technique. In some embodiments, microprocessor 148, FPGA 146, or both, may perform the functions of TPU 158 using suitable timing signals and multiplexing/de-multiplexing algorithms, and accordingly TPU 158 need not be included. The received signal from detector 118 may be passed through amplifier 166, low pass filter 168, and analog-to-digital converter 170. The digital data may then be stored in a queued serial module (QSM) 172 (or buffer such as a first in first out (FIFO) buffer) for later downloading to RAM 128 as QSM 172 fills up. A window of data may be selected from the data stored in the buffer for further processing. In some embodiments, there may be multiple separate parallel paths having components equivalent to amplifier 162, switching circuit 164, amplifier 166, filter 168, and/or A/D converter 170 for multiple light wavelengths or spectra received. In some embodiments, a filter (e.g., an analog filter) may be included (not shown) between amplifier 162 and switching circuit 164.

In some embodiments, microprocessor 148 may determine the subject's physiological parameters, such as pulse rate, $SpO_2$, and/or blood pressure, using various algorithms and/or look-up tables based on the value of the received signals and/or data corresponding to the light received by detector 118. Signals corresponding to information about subject 140, and particularly about the intensity of attenuated light emanating from a subject's tissue over time, may be transmitted from encoder 142 to decoder 174. These signals may include, for example, encoded information relating to subject characteristics. Decoder 174 may translate these signals to enable the microprocessor to determine the thresholds based on algorithms or look-up tables stored in ROM 126. In some embodiments, user inputs 130 may be used to enter information, select one or more options, provide a response, input settings, any other suitable inputting function, or any combination thereof. User inputs 130 may be used to enter information about the subject, such as age, weight, height, diagnosis, medications, treatments, and so forth. In some embodiments, display 120 may exhibit a list of values which may generally apply to the subject, such as, for example, age ranges or medication families, which the user may select using user inputs 130.

Calibration device 180, which may be powered by monitor 114 via a coupling 182, a battery, or by a conventional power source such as a wall outlet, may include any suitable signal calibration device. Calibration device 180 may be communicatively coupled to monitor 114 via communicative coupling 182, and/or may communicate wirelessly (not shown). In some embodiments, calibration device 180 is completely integrated within monitor 114. In some embodiments, calibration device 180 may include a manual input device (not shown) used by an operator to manually input reference signal measurements obtained from some other source (e.g., an external invasive or non-invasive physiological measurement system). Calibration device 180 may be coupled to one or more components of monitor 114 to calibrate monitor 114.

Communications interface 132 may enable monitor 114 to exchange information with external devices. Communications interface 132 may include any suitable hardware, software, or both, which may allow physiological monitoring system 110 (e.g., monitor 114) to communicate with electronic circuitry, a device, a network, or any combinations thereof. Communications interface 132 may include one or more receivers, transmitters, transceivers, antennas, plug-in connectors, ports, communications buses, communications protocols, device identification protocols, any other suitable hardware or software, or any combination thereof. Communications interface 132 may be configured to allow wired communication (e.g., using USB, RS-232, Ethernet, or other standards), wireless communication (e.g., using WiFi, IR, WiMax, BLUETOOTH, UWB, or other standards), or both. For example, communications interface 132 may be configured using a universal serial bus (USB) protocol (e.g., USB 2.0, USB 3.0), and may be configured to couple to other devices (e.g., remote memory devices storing templates) using a four-pin USB standard Type-A connector (e.g., plug and/or socket) and cable. In some embodiments, communications interface 132 may include an internal bus such as, for example, one or more slots for insertion of expansion cards.

Figure 2:
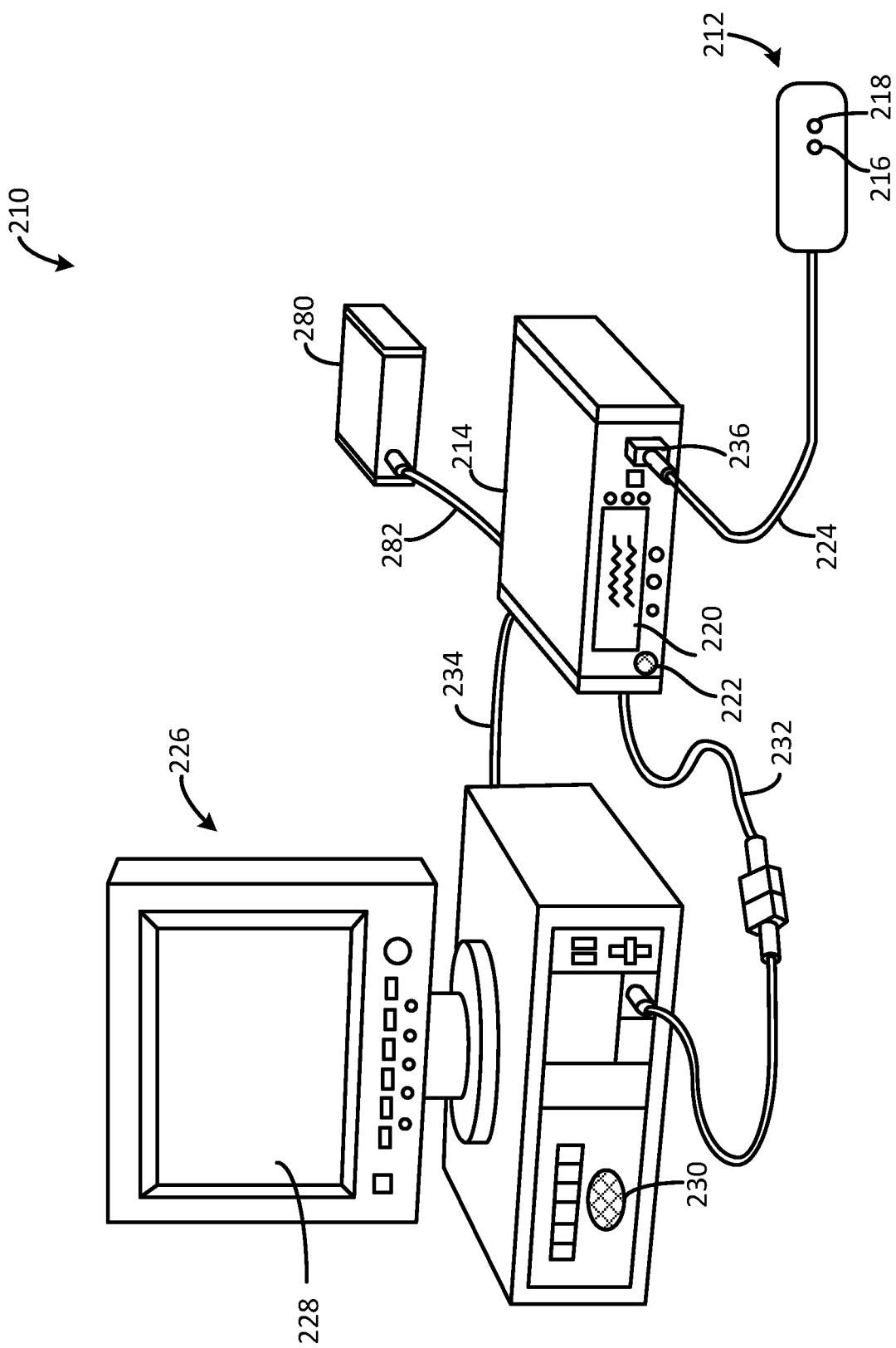
FIG. 2 is a perspective view of an illustrative physiological monitoring system in accordance with some embodiments of the present disclosure.

FIG. 2 is a perspective view of an illustrative physiological monitoring system 210 in accordance with some embodiments of the present disclosure. In some embodiments, one or more components of physiological monitoring system 210 may include one or more components of physiological monitoring system 110 of FIG. 1. Physiological monitoring system 210 may include sensor unit 212 and monitor 214. In some embodiments, sensor unit 212 may be part of a continuous, non-invasive blood pressure (CNIBP) monitoring system and/or an oximeter. Sensor unit 212 may include light source 216 for emitting light at one or more wavelengths into a subject's tissue. Detector 218 may also be provided in sensor unit 212 for detecting the light that is reflected by or has traveled through the subject's tissue. Any suitable configuration of light source 216 and detector 218 may be used. In some embodiments, sensor unit 212 may include multiple light sources and detectors, which may be spaced apart. Physiological monitoring system 210 may also include one or more additional sensor units (not shown) that may, for example, take the form of any of the embodiments described herein with reference to sensor unit 212. An additional sensor unit may be the same type of sensor unit as sensor unit 212, or a different sensor unit type than sensor unit 212. Multiple sensor units may be capable of being positioned at two different locations on a subject's body. For example, a first sensor unit may be positioned on a subject's forehead, while a second sensor unit may be positioned at a subject's fingertip.

Sensor units may each detect any signal that carries information about a subject's physiological state, such as an electrocardiograph signal, arterial line measurements, or the pulsatile force exerted on the walls of an artery using, for example, oscillometric methods with a piezoelectric transducer. According to another embodiment, physiological monitoring system 210 may include a plurality of sensors forming a sensor array in lieu of either or both of the sensor units. Each of the sensors of a sensor array may be a complementary metal oxide semiconductor (CMOS) sensor. Alternatively, each sensor of an array may be a charged coupled device (CCD) sensor. In some embodiments, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. In some embodiments, each pixel may have a photodetector and an active amplifier. In some embodiments, a group of pixels may share an amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, light source 216 and detector 218 may be on opposite sides of a digit such as a finger or toe, in which case the light that is emanating from the tissue has passed completely through the digit. In some embodiments, light source 216 and detector 218 may be arranged so that light from light source 216 penetrates the tissue and is attenuated by the tissue and transmitted to detector 218, such as in a sensor designed to obtain pulse oximetry data from a subject's forehead.

In some embodiments, sensor unit 212 may be connected to and draw its power from monitor 214 as shown. In some embodiments, sensor unit 212 may be wirelessly connected (not shown) to monitor 214 and may be powered by an internal power source such as a battery (not shown). Monitor 214 may be configured to calculate physiological parameters based at least in part on data relating to light emission and detection received from one or more sensor units such as sensor unit 212. For example, monitor 214 may be configured to determine pulse rate, respiration rate, respiration effort, blood pressure, blood oxygen saturation (e.g., arterial, venous, or both), hemoglobin concentration (e.g., oxygenated, deoxygenated, and/or total), any other suitable physiological parameters, or any combination thereof. In some embodiments, calculations may be performed on the sensor units or an intermediate device and the result of the calculations may be passed to monitor 214. Further, monitor 214 may include display 220 configured to display the physiological parameters or other information about the system. In the embodiment shown, monitor 214 may also include a speaker 222 to provide an audible sound that may be used in various other embodiments, such as for example, sounding an audible alarm in the event that a subject's physiological parameters are not within predefined range specified by system process requirements. In some embodiments, monitor 214 may include a blood pressure monitor. In some embodiments, the physiological monitoring system 210 may include a stand-alone blood pressure monitor in communication with the monitor 214 via a cable or a wireless network link. In some embodiments, monitor 214 may be implemented as display 120 of FIG. 1.

In some embodiments, sensor unit 212 may be communicatively coupled to monitor 214 via a cable 224 at port 236. Cable 224 may include electronic conductors (e.g., wires for transmitting electronic signals from detector 218), optical fibers (e.g., multi-mode or single-mode fibers for transmitting emitted light from light source 216), any other suitable components, any suitable insulation or sheathing, or any combination thereof. In some embodiments, a wireless transmission device (not shown) or the like may be used instead of or in addition to cable 224. Monitor 214 may include a sensor interface configured to receive physiological signals from sensor unit 212, provide signals and power to sensor unit 212, or otherwise communicate with sensor unit 212. The sensor interface may include any suitable hardware, software, or both, which may allow communication between monitor 214 and sensor unit 212.

In the illustrated embodiment, physiological monitoring system 210 includes a multi-parameter physiological monitor 226. Multi-parameter physiological monitor 226 may include a cathode ray tube display, a flat panel display (as shown) such as a liquid crystal display (LCD) or a plasma display, or may include any other type of monitor now known or later developed. Multi-parameter physiological monitor 226 may be configured to calculate physiological parameters and to provide a display 228 for information from monitor 214 and from other medical monitoring devices or systems (not shown). For example, multi-parameter physiological monitor 226 may be configured to display pulse rate information from monitor 214, an estimate of a subject's blood oxygen saturation generated by monitor 214, and blood pressure from monitor 214 on display 228. Multi-parameter physiological monitor 226 may include a speaker 230.

Monitor 214 may be communicatively coupled to multi-parameter physiological monitor 226 via a cable 232 or 234 that is coupled to a sensor input port or a digital communications port, respectively and/or may communicate wirelessly (not shown). In addition, monitor 214 and/or multi-parameter physiological monitor 226 may be coupled to a network to enable the sharing of information with servers or other workstations (not shown). Monitor 214 may be powered by a battery (not shown) or by a conventional power source such as a wall outlet.

In some embodiments, physiological monitoring system 210 may include calibration device 280. Calibration device 280, which may be powered by monitor 214, a battery, or by a conventional power source such as a wall outlet, may include any suitable calibration device. Calibration device 280 may be communicatively coupled to monitor 214 via communicative coupling 282, and/or may communicate wirelessly (not shown). In some embodiments, calibration device 280 may be completely integrated within monitor 214. For example, calibration device 280 may take the form of any invasive or non-invasive blood pressure monitoring or measuring system used to generate reference blood pressure measurements for use in calibrating a CNIBP monitoring technique as described herein. Such calibration devices may include, for example, an aneroid or mercury sphygmomanometer and occluding cuff, a pressure sensor inserted directly into a suitable artery of a subject, an oscillometric device or any other device or mechanism used to sense, measure, determine, or derive a reference blood pressure measurement. In some embodiments, calibration device 280 may include a manual input device (not shown) used by an operator to manually input reference signal measurements obtained from some other source (e.g., an external invasive or non-invasive physiological measurement system).

Calibration device 280 may also access reference signal measurements stored in memory (e.g., RAM, ROM, or a storage device). For example, in some embodiments, calibration device 280 may access reference blood pressure measurements from a relational database stored within calibration device 280, monitor 214, or multi-parameter physiological monitor 226. The reference blood pressure measurements generated or accessed by calibration device 280 may be updated in real-time, resulting in a continuous source of reference blood pressure measurements for use in continuous or periodic calibration. Alternatively, reference blood pressure measurements generated or accessed by calibration device 280 may be updated periodically, and calibration may be performed on the same periodic cycle or a different periodic cycle. In some embodiments, reference blood pressure measurements may be generated when recalibration is triggered. For example, recalibration may be triggered based on a change parameter.

In some embodiments, any of the processing components and/or circuits, or portions thereof, of FIGS. 1 and 2, including sensors 112 and 212 and monitors 114, 214, and 226 may be referred to collectively as processing equipment. For example, processing equipment may be configured to amplify, filter, sample and digitize an input signal from sensor 112 or 212 (e.g., using an analog-to-digital converter), calculate metrics from the digitized signal, and trigger a physiological measurement or recalibration. In some embodiments, all or some of the components of the processing equipment may be referred to as a module.

The optical signal attenuated by the tissue can be degraded by noise, among other sources, and an electrical signal derived thereof can also be degraded by noise. One source of noise is ambient light that reaches the light detector. Another source of noise in an intensity signal is electromagnetic coupling from other electronic instruments. Movement of the subject also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial and pressure effects, thus resulting in momentary changes in volume at the point to which the oximeter probe is attached.

Noise (e.g., from subject movement) can degrade a sensor signal relied upon by a clinician, without the clinician's awareness. This is especially true if the monitoring of the subject is remote, the motion is too small to be observed, or the clinician is watching the instrument or other parts of the subject, and not the sensor site. Analog and/or digital processing of sensor signals (e.g., PPG signals) may involve operations that reduce the amount of noise present in the signals or otherwise identify noise components in order to prevent them from affecting measurements of physiological parameters derived from the sensor signals.

It will be understood that the present disclosure is applicable to any suitable signal and that PPG signals are used merely for illustrative purposes. Those skilled in the art will recognize that the present disclosure has wide applicability to other signals including, but not limited to, other biosignals (e.g., electrocardiograms, electroencephalograms, electrogastrograms, electromyograms, pulse rate signals, pathological signals, ultrasound signals, near infrared spectroscopy (NIRS) signals, any other suitable biosignals), or any combination thereof.

Figure 3:
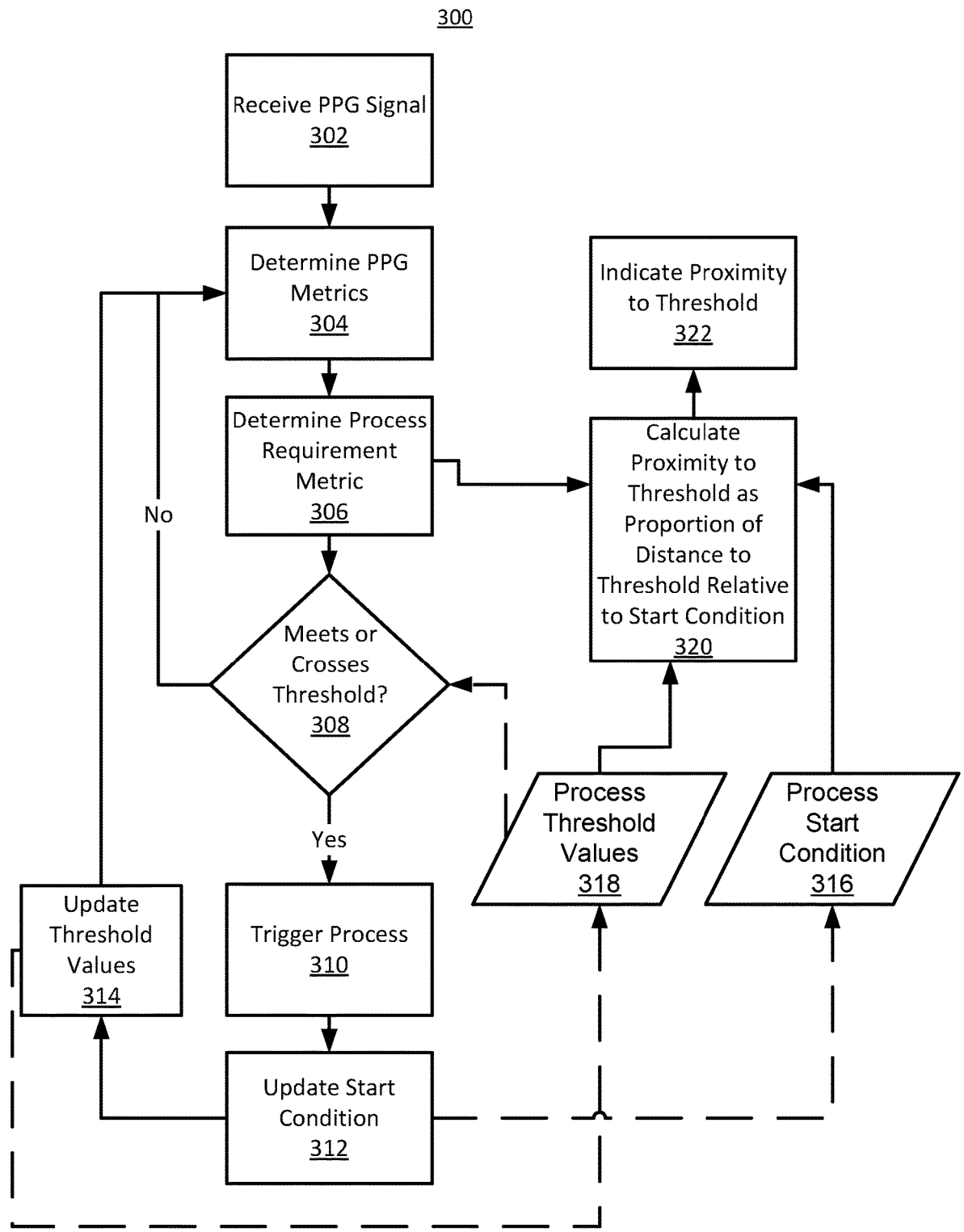
FIG. 3 shows a flow diagram including illustrative steps for determining and indicating the proximity of a process requirement metric to a corresponding system process requirement in accordance with some embodiments of the present disclosure.

FIG. 3 shows a flow diagram including illustrative steps for determining and indicating the proximity of a process requirement metric to a corresponding system process requirement in accordance with some embodiments of the present disclosure.

At step 302, a PPG signal is received. In some embodiments, a monitor, such as monitor 114 of FIG. 1 or monitors 214 or 226 of FIG. 2, may be used to receive the PPG signal. In some embodiments, the PPG signal may have undergone signal processing before being received, such as any suitable band-pass filtering, adaptive filtering, closed-loop filtering, any other suitable filtering, or any combination thereof. In some embodiments, signal processing may be performed on the PPG signal after it has been received. It will be understood that step 302 may include receiving any suitable physiological signal, and it is not limited to receiving a PPG signal. For example, step 302 may include receiving a biopotential signal, pressure signal, impedance signal, temperature signal, acoustic signal, an NIRS signal, any other suitable physiological signal, or any combination thereof.

Step 304 includes determining PPG metrics based on the PPG signal received at step 302. Metrics may include suitable signal values, signal morphologies, output values from suitable operations performed on the signal or other metrics, any other suitable mathematical characterizations, or any suitable combinations thereof. In some embodiments, metrics may be computed from averaged, filtered, scaled, or otherwise processed physiological signals. PPG metrics may specifically characterize the PPG signal, and may be indicative of pulse wave morphology. PPG metrics may include pulse period, peak to peak amplitude, DC value, percent modulation, skew of the first derivative of the pulse, path ratio, any other suitable characterizations, or any combination thereof. For example, a PPG metric may be the skew of the derivative of a suitable ensemble average of pulse waves. The term "pulse wave" as used herein refers to a portion of a PPG signal corresponding to a physiological pulse. It should be understood that metrics may be determined based on any physiological signal received, and are not limited to PPG metrics based on a PPG signal.

Step 306 includes determining a process requirement metric. A process requirement metric may be indicative of the need to trigger a system process (e.g., an alarm, a recalibration, a measurement, or any combination thereof). A process requirement metric may be any suitable metric or a combination of more than one suitable metrics. Any suitable technique of combining metrics may be used, including weighted sums, non-parametric Bayesian estimates, Neural networks, polynomial function estimates, rule based systems, adaptive rule based systems such as propositional logic or predicate calculus, modal logic, non-monotonic logic, fuzzy logic, any other suitable means, or combination thereof. For example, a process requirement metric may be a combination of a pulse period PPG metric, a percent modulation PPG metric, a skew derivative PPG metric, and a DC value PPG metric. In some embodiments, a process requirement metric may also be a change in a metric, for example, a change in a morphology metric characterizing a physiological signal. As used herein, the term "process requirement metric" shall be understood to include within its scope any suitable change in any suitable metric. It should be understood that a process requirement metric may be determined based on metrics which characterize any suitable physiological signal, and need not be determined based on PPG metrics. Additionally, it should be understood that step 306 may include determining more than one process requirement metric.

Step 308 includes determining whether the process requirement metric determined at step 306 has met or crossed a corresponding threshold. The corresponding threshold may be, for example, a default threshold for the process requirement metric determined at step 306, a previously determined threshold for the process requirement metric determined at step 306, a threshold specified by a clinician, any other suitable threshold, or any combination thereof. When the process requirement metric reaches a value that is equal to or has crossed the corresponding threshold, a system process may be triggered. A system process may be an alarm, a recalibration, a measurement, any other suitable system process, or any combination thereof. For example, the corresponding threshold may be an upper threshold limit which is used to trigger a measurement in an NIBP system when the process requirement metric value meets or crosses the threshold limit. The triggered measurement may be used, for example, as an updated measurement for a monitored patient or as a part of a system recalibration. The corresponding threshold need not be limited to an upper threshold limit, but may also refer to a lower threshold limit for the process requirement metric, or any other suitable system process requirement, or any combination thereof. For example, the corresponding threshold may be a lower threshold limit which is used to trigger an alarm in a pulse oximetry system when the $SpO_2$ value is at or below the threshold limit. If it is determined that the process requirement metric has met or crossed the corresponding threshold at step 308, processing may proceed to step 310, which includes triggering the system process triggered by the corresponding threshold. Subsequently, processing may proceed to steps 312 and 314, which include updating a start condition and corresponding threshold for the process requirement metric respectively. A start condition may be a start value of the process requirement metric, and may be used to normalize a change in the process requirement metric. For example, if a start value for a process requirement metric is known, a percentage change in the process requirement metric value may be determined and compared to a corresponding threshold. The corresponding threshold updated at step 314 may be updated based on the start condition updated at step 312. For example, if a start value of a process requirement metric is updated, a corresponding threshold may be updated to account for the updated start value and correctly reflect the necessary process requirement metric value to trigger a system process. The start condition and corresponding threshold updated at steps 312 and 314 respectively are processed at steps 316 and 318 respectively. The corresponding threshold updated at step 314 and processed at step 318 may be subsequently used at step 308 to determine whether or not the process requirement metric has met or crossed the corresponding threshold. It should be understood that step 308 may include comparing more than one process requirement metric determined at step 306 to more than one corresponding threshold. Additionally, step 310 may include triggering more than one system process based on more than one corresponding threshold, and steps 312 and 314 may respectively include updating more than one start condition and more than one threshold corresponding to more than one process requirement metric determined at step 306.

If it is determined that the process requirement metric has not met or crossed the corresponding threshold at step 308, processing may repeat steps 304 through 308 until the process requirement metric meets or crosses the corresponding threshold.

Step 320 includes calculating the proximity of the process requirement metric to the corresponding threshold. The proximity may be calculated at step 320 each time the process requirement metric is determined at step 306. The start condition for the process requirement metric, updated at step 312 and processed at step 316, and the corresponding threshold for the process requirement metric, updated at step 314 and processed at step 318, may be used to calculate the proximity. For example, the proximity of the process requirement metric to the corresponding threshold may be calculated based on a proportion of the change in the process requirement relative to the start condition of the process requirement metric. Step 322 includes indicating the proximity calculated at step 320. The proximity may be indicated, for example, on a display such as display 120 of FIG. 1 or displays 220 or 228 of FIG. 2. It should be understood that step 320 may include calculating more than one proximity of more than one process requirement metric to more than one corresponding threshold, and that step 322 may include indicating more than one proximity calculated at step 320. It will be understood that steps 302 through 322 may be equally applied to any medical device which includes processes triggered through a conditional operator with reference to a threshold value, or any other suitable system process requirement.

Figure 4:
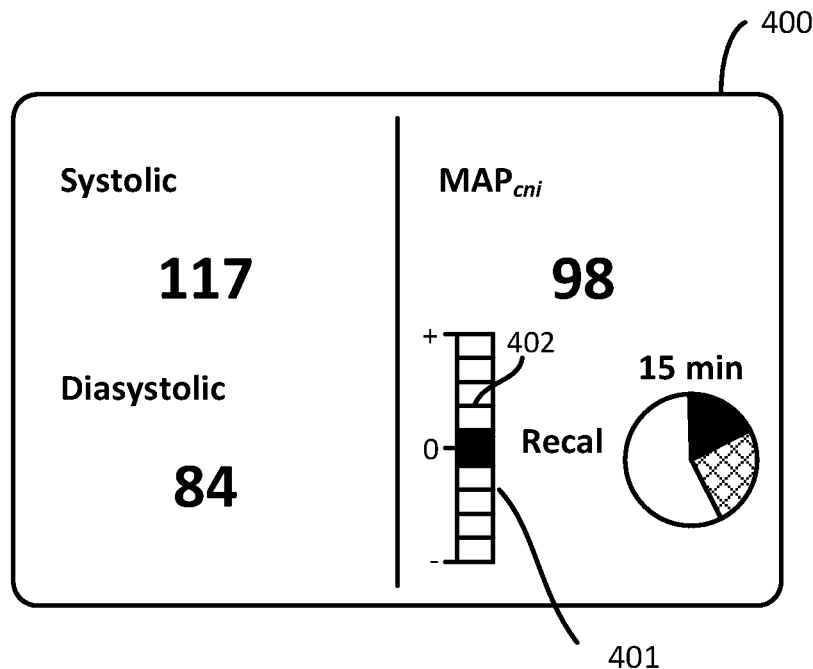
FIG. 4 shows an illustrative display of a physiological monitor including a bar display for indicating the proximity of a process requirement metric to a corresponding system process requirement in accordance with some embodiments of the present disclosure.

FIG. 4 shows an illustrative display of a physiological monitor including a bar display for indicating the proximity of a process requirement metric to a corresponding system process requirement in accordance with some embodiments of the present disclosure.

Figure 8:
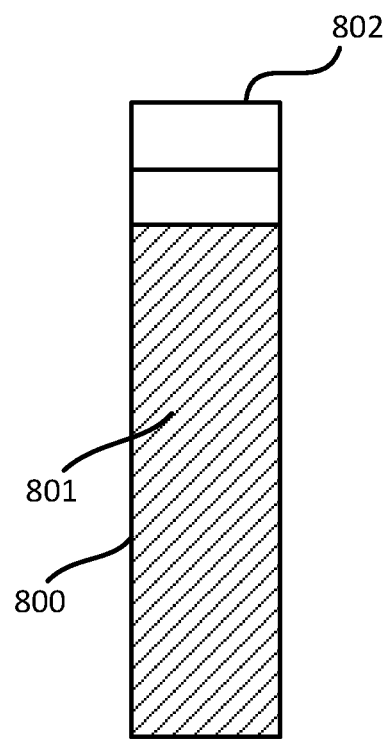
FIG. 8 shows an illustrative bar display for indicating the proximity of a process requirement metric to a corresponding system process requirement in accordance with some embodiments of the present disclosure.
Figure 9:
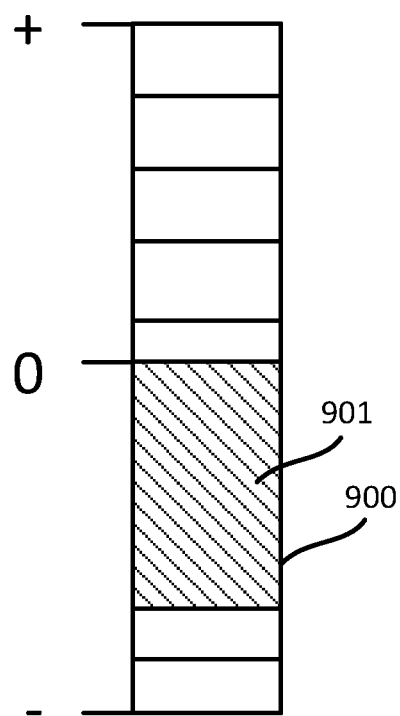
FIG. 9 shows another illustrative bar display for indicating the proximity of a process requirement metric to a corresponding system process requirement in accordance with some embodiments of the present disclosure.

Display 400 is an illustrative physiological monitor display including exemplary bar display 401 for indicating the proximity of a process requirement metric to a corresponding system process requirement (e.g., a threshold). When the process requirement metric reaches a value that is equal to or has crossed the system process requirement, a system process (e.g., a recalibration, a measurement, an alarm, or any combination thereof) may be triggered. For example, bar display 401 may represent the proximity of a process requirement metric to a corresponding threshold which triggers a measurement when the value of the process requirement metric meets or crosses the corresponding threshold. The circular indicator to the right of bar display 401 may represent a timed trigger which triggers a system process if the process requirement metric does not reach a value that is equal to or exceeds the system process requirement within the time limit displayed by the circular indicator. The top and bottom of bar display 401, marked with a '+' and a '−' in FIG. 4, may represent current upper and lower system process requirements respectively. Upper and lower system process requirements may trigger the same system process, or may trigger different system processes. For example, upper and lower system process requirements may both trigger a measurement via cuff inflation in a non-invasive blood pressure monitoring system. Grid lines 402 may represent possible values of the process requirement metric which the proximity indicated in bar display 401 is based on. The process requirement metric may also have values which are in between or outside of grid lines 402. Grid lines 402 may allow a user or a clinician to graphically estimate the value of the process requirement metric. Grid lines 402 may also allow a user or a clinician to graphically estimate changes in the proximity of the process requirement metric to a corresponding system process requirement. The center of bar display 401, marked with a '0', may represent the start condition of the process requirement metric which the proximity indicated in bar display 401 is based on. The start condition may be, for example, a start value of the process requirement metric. The start value need not be zero, and may be any suitable value marked by any suitable marker, or not marked at all. The black indication bar shown at the center of bar display 401 may indicate the current value of the process requirement metric which the proximity indicated in bar display 401 is based on. The black indication bar may be located at any suitable position within bar display 401 to indicate to value of the process requirement metric, and may change position as the value of the process requirement metric changes. The position of the black indication bar may also represent a change in value of the process requirement metric, and the change may be calculated with respect to a start value for the process requirement metric. For example, the black indication bar may represent the percentage change in a process requirement metric. Bar display 401 is merely an exemplary means of indicating proximity on a physiological monitor display, such as display 400. In some embodiments, display 400 may be display 120 of FIG. 1 or displays 220 or 228 of FIG. 2, and may be included in a monitor, for example, monitor 114 of FIG. 1 or monitors 214 or 226 of FIG. 2. It should be understood that proximity may be indicated on any physiological monitor in any suitable manner. For example, an indication of proximity of a process requirement metric to a corresponding system process requirement may comprise a colored bar display, and the color of the bar display may be indicative of the magnitude of the proximity. Additional examples of indicating proximity of a process requirement metric to a corresponding system process requirement are shown in FIG. 8 and FIG. 9 of the present disclosure. It should be understood that indicating proximity need not include a graphical display. For example, proximity may be indicated by presenting aural cues. Aural cues may be presented using a speaker, for example, speaker 122 of FIG. 1 or speakers 222 or 230 of FIG. 2. In one embodiment, the pitch of aural cues is based on the proximity. In another embodiment, aural cues may include tonal beeps, and the duration of the tonal beeps may be based on the proximity.

Figure 5:
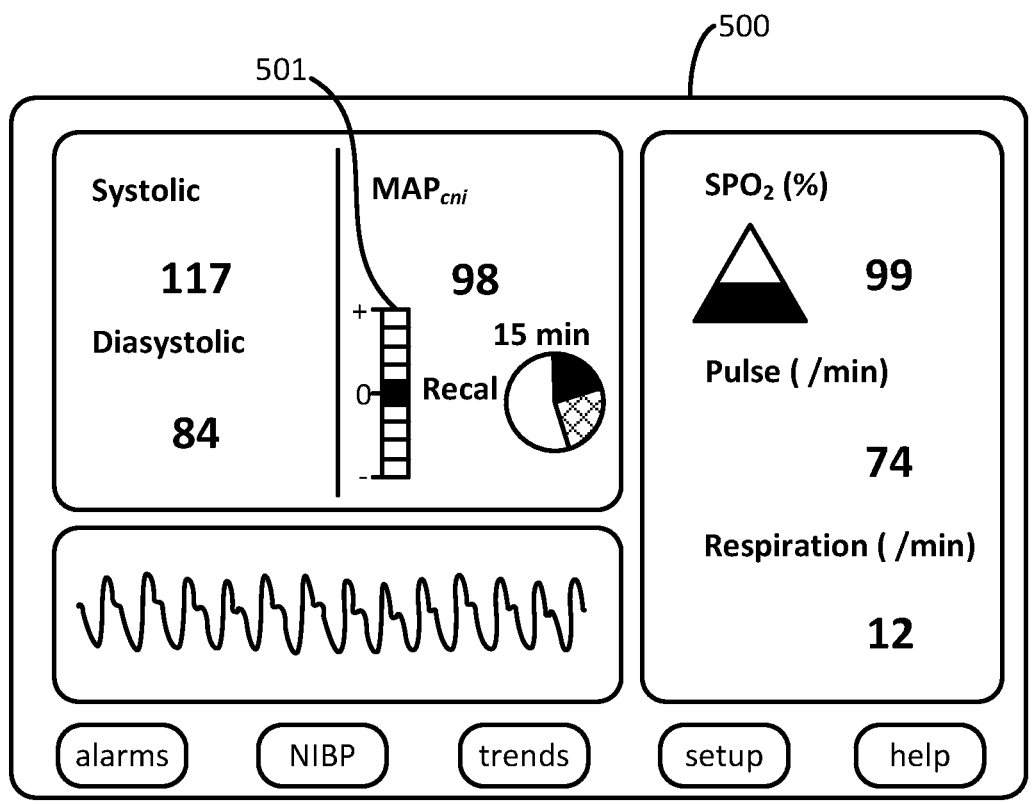
FIG. 5 shows an illustrative multiparametric display of a physiological monitor including a bar display for indicating the proximity of a process requirement metric to a corresponding system process requirement in accordance with some embodiments of the present disclosure.

FIG. 5 shows an illustrative multiparametric display of a physiological monitor including a bar display for indicating the proximity of a process requirement metric to a corresponding system process requirement in accordance with some embodiments of the present disclosure.

Multiparametric display 500 is an illustrative physiological monitor display including exemplary bar display 501 for indicating the proximity of a process requirement metric to a corresponding system process requirement (e.g. a threshold). When the process requirement metric reaches a value that is equal to or has crossed the system process requirement, a system process (e.g., a recalibration, a measurement, an alarm, or any combination thereof) may be triggered. Bar display 501 may represent, for example, the proximity of a process requirement metric to a threshold which triggers a measurement when the value of the process requirement metric meets or crosses the threshold. The circular indicator to the right of bar display 501 may represent a timed trigger which triggers a system process if the process requirement metric does not reach a value that is equal to or exceeds the system process requirement within the time limit displayed by the circular indicator. Bar display 501 as shown in FIG. 5 only occupies a portion of multiparametric display 500. It should be understood that this view is only exemplary, and that bar display 501 may be displayed in any suitably sized portion of multiparametric display 500. Display 500 may be included in a monitor, for example, monitor 114 of FIG. 1 or monitors 214 or 226 of FIG. 2. It should be understood that bar display 501 is only an exemplary indication of proximity. Proximity of a process requirement metric to a corresponding system process requirement may be indicated in any suitable manner, including a bar display, a color changing display, aural cues, any other suitable manner, or any combination thereof.

Figure 6:
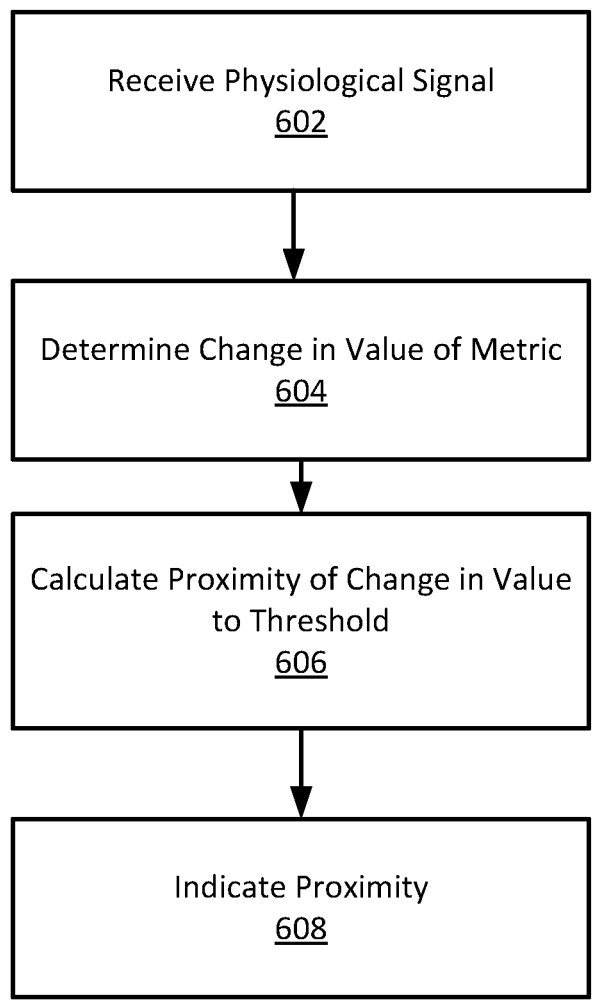
FIG. 6 is a flow diagram including illustrative steps for indicating the proximity of a process requirement metric to a corresponding system process requirement in accordance with some embodiments of the present disclosure.

FIG. 6 is a flow diagram including illustrative steps for indicating the proximity of a process requirement metric to a corresponding system process requirement in accordance with some embodiments of the present disclosure.

At step 602 a physiological signal is received (e.g. a PPG signal). In some embodiments, a monitor, such as monitor 114 of FIG. 1 or monitors 214 or 226 of FIG. 2, may be used to receive the physiological signal. In some embodiments, the physiological signal may have undergone signal processing before being received, such as any suitable band-pass filtering, adaptive filtering, closed-loop filtering, any other suitable filtering, or any combination thereof. In some embodiments, signal processing may be performed on the physiological signal after it has been received. Step 602 may include receiving any suitable physiological signal, and it is not limited to receiving a PPG signal. For example, step 602 may include receiving a biopotential signal, pressure signal, impedance signal, temperature signal, acoustic signal, NIRS signal, any other suitable physiological signal, or any combination thereof.

Step 604 includes determining a change in value of at least one metric based on the physiological signal received at step 602. Metrics may include suitable signal values, signal morphologies, output values from suitable operations performed on the signal or other metrics, any other suitable mathematical characterizations, or any suitable combinations thereof. In some embodiments, metrics may be computed from averaged, filtered, scaled, or otherwise processed physiological signals. For example, a metric may be heart rate, $SpO_2$, blood pressure, any other suitable characteristic, or any combination thereof. Determining a change in value of a metric may be done with processing equipment. For example, determining a change in value of a metric may be done with a metric module. The change in value of a metric may be determined based on a start condition of the metric, for example, a start value. For example, step 604 may include determining a change in $SpO_2$.

Step 606 includes calculating the proximity of the change in value of a metric determined in step 604 to a corresponding threshold. When the change in value meets or crosses the corresponding threshold, a system process (e.g., a recalibration, a measurement, an alarm, or any combination thereof) may be triggered. For example, step 602 may include receiving a PPG signal, step 404 may include determining a change in a peak to peak amplitude metric based on the received PPG signal and one or more previous values of the peak to peak amplitude metric, and step 606 may include calculating the proximity of the change to a corresponding threshold, or any other suitable system process requirement, where a measurement is triggered when the change meets or crosses the corresponding threshold. In another example, step 602 may include receiving a PPG signal, step 404 may include determining a change in blood pressure based on the received PPG signal and one or more previous values of blood pressure, and step 606 may include calculating the proximity of the change to a corresponding threshold, where the corresponding threshold triggers a recalibration when the change equals or crosses the corresponding threshold. The proximity may be calculated using processing equipment, for example, a proximity module.

Step 608 includes indicating the proximity calculated at step 606. The proximity may be indicated on a display of a physiological monitor, for example, monitor 114 of FIG. 1 or monitors 214 or 226 of FIG. 2. For example, the proximity may be indicated by bar display 401 or bar display 501. The proximity may also be indicated, for example, by aural cues, by a color changing display, by any other suitable manner of indication, or any combination thereof, and is not limited to being displayed.

Figure 7:
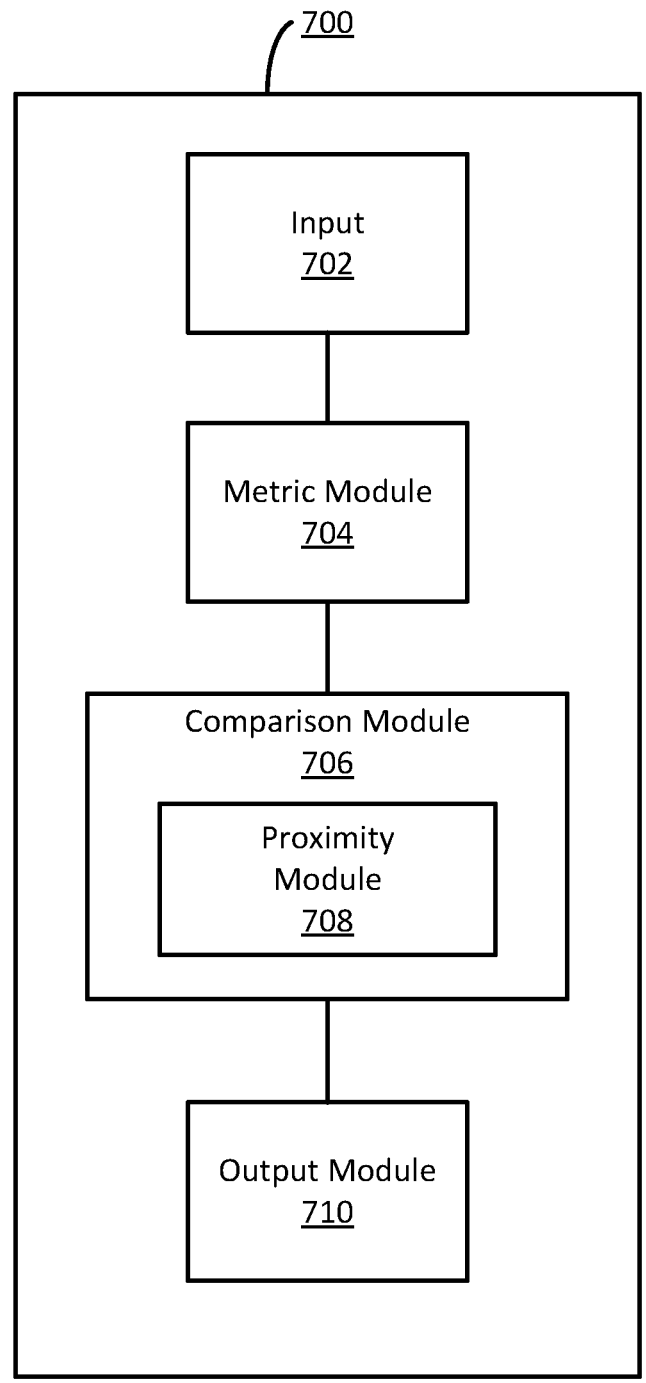
FIG. 7 is a block diagram of an illustrative system for indicating the proximity of a process requirement metric to a corresponding system process requirement in accordance with some embodiments of the present disclosure.

FIG. 7 is a block diagram including an illustrative system for indicating the proximity of a process requirement metric to a corresponding system process requirement in accordance with some embodiments of the present disclosure.

System 700 is an illustrative system which may indicate the proximity of a process requirement metric to a corresponding system process requirement (e.g. a threshold). System 700 may include input 702, which may be configured to receive a physiological signal. Input 702 may be configured to receive a PPG signal, or any other physiological signal, for example, a biopotential signal, pressure signal, impedance signal, temperature signal, acoustic signal, NIRS signal, any other suitable physiological signal, or any combination thereof. In some embodiments, the physiological signal may have undergone signal processing before being received by input 702, such as any suitable band-pass filtering, adaptive filtering, closed-loop filtering, any other suitable filtering, or any combination thereof. In some embodiments, signal processing may be performed on the physiological signal after it has been received by input 702. In some embodiments, input 702 may be a sensor signal input to a monitor (or any suitable pre-processed sensor signal input to processing circuitry of a monitor), such as monitor 114 of FIG. 1 or monitors 214 or 226 of FIG. 2.

Metric module 704 of system 700 may be coupled to input 702, and may be configured to determine a value of a process requirement metric based on the physiological signal received at input 702. The process requirement metric may be any metric or combination of metrics, and may characterize the received physiological signal. Metrics may include suitable signal values, signal morphologies, output values from suitable operations performed on the signal or other metrics, any other suitable mathematical characterizations, or any suitable combinations thereof. In some embodiments, metrics may be computed from averaged, filtered, scaled, or otherwise processed physiological signals. Any suitable means of combining metrics may be used, including weighted sums, non-parametric Bayesian estimates, Neural networks, polynomial function estimates, rule based systems, adaptive rule based systems such as propositional logic or predicate calculus, modal logic, non-monotonic logic, fuzzy logic, any other suitable means, or combination thereof. For example, metric module 704 may determine a process requirement metric which is a weighted sum of the pulse period and percent modulation of a received PPG signal. In some embodiments, metric module 704 may be any suitable software, hardware, or both configured to implement the features as described herein. For example, metric module 704 may be at least partially implemented as part of a processor such as microprocessor 148 of FIG. 1. In other embodiments, metric module 704 may be a monitor such as monitor 114 of FIG. 1 or monitors 214 or 226 of FIG. 2.

Comparison module 706 of system 700 may be coupled to metric module 704, and may be configured to compare the value of a process requirement metric to a corresponding threshold. For example, comparison module 706 may be configured to compare a pulse period metric, determined by metric module 704 and based on a PPG signal received by input 702, to a corresponding upper threshold limit for the pulse period of a PPG signal. In some embodiments, comparison module 706 may be configured to output a comparison signal based on the comparison. The output comparison signal may be useable to trigger a system process (e.g., a measurement, a recalibration, an alarm, or any combination thereof) when the value of the process requirement metric meets or crosses the corresponding threshold. In some embodiments, comparison module 706 may be any suitable software, hardware, or both configured to implement the features as described herein. For example, comparison module 706 may be at least partially implemented as part of a processor such as microprocessor 148 of FIG. 1. In other embodiments, comparison module 706 may be a monitor such as monitor 114 of FIG. 1 or monitors 214 or 226 of FIG. 2.

Comparison module 706 of system 700 may include proximity module 708. Proximity module 708 may be configured to calculate the proximity of a value of a process requirement metric to a corresponding threshold. When the process requirement metric reaches a value that is equal to or has crossed the corresponding threshold, a system process (e.g., a measurement, a recalibration, an alarm, or any combination thereof) may be triggered. A system process may be triggered by a clinician or by any suitable software, hardware, or both, within or external to, system 700. For example, in some embodiments system 700 may include a measurement module and a system process may be triggered by the measurement module. In some embodiments, the corresponding threshold may be updated before or after a system process is triggered, for example, based on the proximity calculated by proximity module 708. The proximity calculated by proximity module 708 may be indicated to a user using an output module, such as output module 710. In some embodiments, proximity module 708 may be any suitable software, hardware, or both configured to implement the features as described herein. For example, proximity module 708 may be at least partially implemented as part of a processor such as microprocessor 148 of FIG. 1. In other embodiments, proximity module 708 may be a monitor such as monitor 114 of FIG. 1 or monitors 214 or 226 of FIG. 2.

Output module 710 may be coupled to comparison module 706, proximity module 708, or both, and may be configured to indicate the proximity of a value of a process requirement metric to a corresponding threshold. The proximity indicated by output module 710 may be the proximity calculated by proximity module 708. Output module 710 may be configured to indicate proximity on a graphical display, through the presentation of aural cues, in any other suitable manner of indication, or any combination thereof. In some embodiments, output module 710 can be any suitable software, hardware, or both for providing an indication of the calculated proximity. For example, output module 710 can be display equipment (e.g., display 120 of FIG. 1 or displays 220 or 228 of FIG. 2), audio equipment (e.g., speaker 122 of FIG. 1 or speakers 222 or 230 of FIG. 2), any other suitable output device, or any combination thereof. In some embodiments, more than one process requirement metric value is determined by metric module 704, each determined process requirement metric value is compared to a corresponding threshold by comparison module 706, a proximity of each process requirement metric value to its corresponding threshold is calculated by proximity module 708, and one or more of these calculated proximities is indicated by output module 710. Output module 710 may choose to indicate one proximity value from multiple calculated proximity values based on magnitude, predefined priorities, any other suitable characteristic, or any combination thereof. Alternatively, output module 710 may indicate an average of multiple calculated proximity values. For example, metric module 704 may determine three process requirement metrics, proximity module 708 may calculate the proximity of each determined process requirement metric to a corresponding threshold, and output module 710 may indicate the highest magnitude proximity. However, output module 710 is not limited to indicating only one proximity value, and may be configured to indicate multiple calculated proximity values. In some embodiments, output module 710 may be configured to indicate a trend of proximity values over time. For example, proximity module 708 may be configured to calculate proximity values for one or more values of a process requirement metric to one or more values of a corresponding threshold, and the resulting proximity values may be displayed by output module 710 in any suitable manner, including, for example, a graph of proximity values versus time which displays the trending behavior of the calculated proximity values over time. In some embodiments, system 700 may be configured to trigger an alarm when a series of calculated proximity values are within a predetermined percentage of a corresponding threshold for a predetermined amount of time. For example, if a series of proximity values corresponding to the proximity of a patient's blood pressure to a corresponding threshold are within five percent of the threshold for a predetermined time limit of one minute, an alarm may be triggered.

FIG. 8 shows an illustrative bar display for indicating the proximity of a process requirement metric to a corresponding system process requirement in accordance with some embodiments of the present disclosure.

Bar display 800 of FIG. 8 is an exemplary way of indicating the proximity of a process requirement metric to a corresponding system process requirement (e.g., a threshold). When the process requirement metric reaches a value that is equal to or has crossed the system process requirement, a system process (e.g., a measurement, a recalibration, an alarm, or any combination thereof) may be triggered. Proximity may be calculated, for example, by proximity module 708 of system 700. For example, bar display 800 may indicate the proximity between blood pressure, and an upper threshold for blood pressure. Top 802 of bar display 800 may represent the current system process requirement (e.g., threshold) corresponding to the process requirement metric. For example, top 802 of bar display 800 may represent an upper threshold which triggers an alarm. Bar display 800 may include a shaded portion 801, the height of which may indicate the value of the process requirement metric. The height of shaded portion 801 may alternatively indicate the magnitude of proximity to a system process requirement. Shaded portion 801 may fill from the bottom, and grow larger as the value of the process requirement metric increases. Shaded portion 801 may alternatively fill from the top, increase, decrease, change in any other suitable manner, or any combination thereof, to indicate the value of the process requirement. Bar display shaded portion 801 need not use shading to represent the value of the process requirement metric, but may change in color, width, any other suitable characteristic, or combination thereof to indicate the value. Bar display 800 may include visual grid lines, which may be used to estimate the height of shaded portion 801 or the proximity of the process requirement metric to the corresponding system process requirement. For example, if bar display 800 represents the proximity of a subject's blood pressure to a blood pressure threshold, the proximity of the subject's blood pressure to the corresponding blood pressure threshold may be estimated by a clinician by looking at the height of shaded portion 801 in relation to the nearest grid line and top 802 of bar display 800.

FIG. 9 shows another illustrative bar display for indicating the proximity of a process requirement metric to a corresponding system process requirement in accordance with some embodiments of the present disclosure.

Bar display 900 of FIG. 9 is an exemplary way of indicating the proximity of a process requirement metric to at least one corresponding system process requirement (e.g., a threshold). When the process requirement metric reaches a value equal to a system process requirement, a system process (e.g., a measurement, a recalibration, an alarm, or any combination thereof) may be triggered. Proximity may be calculated, for example, by proximity module 708 of system 700. For example, bar display 900 may indicate the proximity of a subject's blood pressure to corresponding upper and lower blood pressure thresholds. The top of bar display 900, marked with a '+', may represent an upper system process requirement which triggers a system process. Similarly, the bottom of bar display 900, marked with a '−', may represent a lower system process requirement which triggers a system process. For example, the top of bar display 900 may represent an upper threshold for blood pressure which triggers a recalibration when met or crossed, and the bottom of bar display 900 may represent a lower threshold for blood pressure which also triggers a recalibration when met or crossed. Upper and lower system process requirements need not trigger the same system process, but may alternatively trigger different system processes. The center of bar display 900, marked with a '0', may indicate the start condition of a process requirement metric. The start condition indicated at the center of bar display 900 may be a start value. The start condition need not be zero, and may be any suitable condition marked by any suitable marker, or not marked at all. For example, the center of bar display 900 may represent an initial blood pressure value. Bar display 900 may include a shaded portion 901, the height of which may represent the value of the process requirement metric. Shaded portion 901 may alternatively indicate the magnitude of the proximity of the process requirement metric to the corresponding system process requirement. Shaded portion 901 may start from the start condition at the center of bar display 900, and may increase towards the top of bar display 900 as the value of the process requirement metric increases, or increase towards the bottom of bar display 900 as the value of the process requirement metric decreases. Shaded bar display portion 901 may alternatively fill, increase, decrease, change in any other suitable manner, or any combination thereof to indicate the value of the process requirement metric. Bar display shaded portion 901 need not use shading to represent the value of the process requirement metric, but may change in color, width, height, or any other suitable characteristic, or combination thereof to indicate the value. Bar display 900 may include visual grid lines. Visual grid lines may be used to graphically estimate the height of shaded portion 901 or the proximity of the process requirement metric to the corresponding system process requirement. For example, if bar display 900 represents the proximity of blood pressure to upper and lower blood pressure thresholds, blood pressure may be estimated by a clinician by looking at the top or bottom of shaded bar display portion 901 in relation to the nearest grid line, the start condition, and the nearest threshold.

It will be understood that the steps above are exemplary and that in some implementations, steps may be added, removed, omitted, repeated, reordered, modified in any other suitable way, or any combination thereof.

The foregoing is merely illustrative of the principles of this disclosure, and various modifications may be made by those skilled in the art without departing from the scope of this disclosure. The above-described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof.

What is claimed is:

1. A system comprising:
 a physiological monitor comprising:
  a display; and
  a processor configured to:
   determine a start condition for a blood pressure metric of a patient based at least in part on at least one physiological signal,
   determine a change over time in a value of the blood pressure metric from the start condition,
   calculate a proximity value indicative of a proximity of the change in the value of the blood pressure metric to a recalibration threshold prior to determining that the change in the value of the blood pressure metric meets or crosses the recalibration threshold,
   initiate recalibration of the physiological monitor by at least updating the recalibration threshold in response to determining that the change in the value of the blood pressure metric meets or crosses the recalibration threshold, and
   indicate, based on the proximity value, the proximity on the display.

2. The system of claim 1, further comprising an input configured to receive the at least one physiological signal from a physiological sensor coupled to the patient, wherein the processor is coupled to the input.

3. The system of claim 1, wherein the processor is configured to determine the change over time in the value of the blood pressure metric based on a morphology metric of the at least one physiological signal.

4. The system of claim 1, wherein the at least one physiological signal comprises a photoplethysmograph signal, a biopotential signal, a pressure signal, an impedance signal, a temperature signal, an acoustic signal, a near-infrared spectroscopy signal, or any combination thereof.

5. The system of claim 4, wherein the processor is configured to determine the change over time in the value of the blood pressure metric based on at least one metric selected from the group consisting of pulse period, peak to peak amplitude, DC value, percent modulation, skew, path ratio, and any combination thereof.

6. The system of claim 1, wherein the processor is configured to trigger an alarm in response to determining that the change in the value of the blood pressure metric met or crossed the recalibration threshold.

7. The system of claim 1, wherein the processor is configured to initiate recalibration by at least initiating a measurement of a physiological parameter in response to determining that the change in the value of the blood pressure metric met or crossed the recalibration threshold.

8. The system of claim 1, further comprising a calibration device, wherein the processor is configured to initiate recalibration by causing the calibration device to measure a physiological parameter.

9. The system of claim 1, wherein the processor is configured to indicate the proximity on the display by at least displaying a bar display that indicates the proximity.

10. The system of claim 9, wherein the bar display comprises a colored bar display, wherein a color of the bar display is indicative of a magnitude of the proximity.

11. The system of claim 1, wherein the processor is configured to indicate the proximity by at least generating a signal indicative of aural cues.

12. A system, comprising:
a display; and
a processor configured to:
determine a start condition for a blood pressure metric of a patient based at least in part on at least one physiological signal,
compare a change in time in a value of the blood pressure metric from the start condition to a recalibration threshold,
output a comparison signal based on the comparison,
calculate a proximity value indicative of a proximity of the change in the value of the blood pressure metric to the recalibration threshold prior to determining that the change in the value of the blood pressure metric meets or crosses the recalibration threshold,
trigger a process in response to determining that the change in the value of the blood pressure metric meets or crosses the recalibration threshold,
after triggering the process, update the recalibration threshold, and
indicate, based on the proximity value, the proximity on the display.

13. The system of claim 12, further comprising an input configured to receive the at least one physiological signal from a physiological sensor coupled to the patient, wherein the processor is coupled to the input.

14. The system of claim 12, wherein the processor is configured to determine the change over time in the value of the blood pressure metric based on a morphology metric of the at least one physiological signal.

15. The system of claim 12, wherein the at least one physiological signal comprises a photoplethysmograph signal, a biopotential signal, a pressure signal, an impedance signal, a temperature signal, an acoustic signal, a near-infrared spectroscopy signal, or any combination thereof.

16. The system of claim 15, wherein the processor is configured to determine the change over time in the value of the blood pressure metric based on at least one metric selected from the group consisting of pulse period, peak to peak amplitude, DC value, percent modulation, skew, path ratio, and any combination thereof.

17. The system of claim 12, wherein the process comprises a measurement of a physiological parameter.

18. The system of claim 12, wherein the processor is configured to indicate the proximity on the display by at least displaying a bar display that indicates the proximity.

19. The system of claim 12, wherein the processor is configured to indicate the proximity by at least generating a signal indicative of aural cues.

* * * * *